United States Patent [19]

Polaschegg et al.

[11] Patent Number: 4,552,552
[45] Date of Patent: Nov. 12, 1985

[54] PUMP SYSTEM FOR USE WITH DIALYSIS AND LIKE APPARATUS

[75] Inventors: Hans-Dietrich Polaschegg, Oberursel; Bernd Mathieu, Spiesen, both of Fed. Rep. of Germany

[73] Assignee: Fresenius AG, Fed. Rep. of Germany

[21] Appl. No.: 466,645

[22] Filed: Feb. 15, 1983

[30] Foreign Application Priority Data

Feb. 16, 1982 [DE] Fed. Rep. of Germany ....... 3205449

[51] Int. Cl.[4] ............................................. A61M 1/03
[52] U.S. Cl. ......................................... 604/4; 604/9;
604/31; 128/1 D; 422/44; 210/321.2
[58] Field of Search ............... 417/317, 394, 478, 479;
604/4, 8, 9, 28, 29, 31, 67, 118, 119; 128/DIG.
3, 1 D, 28, 30; 422/44; 210/321.2

[56] References Cited

U.S. PATENT DOCUMENTS

| 2,822,803 | 2/1958 | Huxley, III et al. | 128/30 |
|---|---|---|---|
| 3,208,448 | 9/1965 | Woodward | 128/DIG. 3 |
| 3,604,016 | 9/1971 | Robinson | 3/1 |
| 3,766,567 | 10/1974 | Kahn et al. | 3/1 |
| 3,791,767 | 2/1974 | Shill | 417/389 |
| 3,811,800 | 5/1974 | Shill | 417/317 |
| 3,883,272 | 5/1975 | Puckett | 128/DIG. 3 |
| 3,891,767 | 2/1974 | Shill | 417/389 |
| 3,955,557 | 5/1976 | Takagi | 128/DIG. 3 |
| 4,023,468 | 5/1977 | Poirier | 92/13.2 |
| 4,133,616 | 1/1979 | Poirier | 417/384 |
| 4,250,872 | 2/1981 | Tamari | 128/1 D |

FOREIGN PATENT DOCUMENTS

| 2417900 | 10/1974 | Fed. Rep. of Germany . |
|---|---|---|
| 2340755 | 2/1975 | Fed. Rep. of Germany . |
| 2455917 | 12/1975 | Fed. Rep. of Germany . |
| 2636290 | 2/1978 | Fed. Rep. of Germany . |

OTHER PUBLICATIONS

The Lancet, Jan. 25, 1958, p. 197.
The New England Journal of Medicine; "Spillation and Migration of Silicone from Blood-Pump Tubing in Patients on Hemodialysis".
Forum Medicotechnicum, 26, Jahrgang, Nr. 12-P. Novak, H. D. Liess, "Ein neues Heimdialysegeriat".

Primary Examiner—C. Fred Rosenbaum
Assistant Examiner—Mario Costantino
Attorney, Agent, or Firm—Finnegan, Henderson, Farabow, Garrett & Dunner

[57] ABSTRACT

The present invention is with respect to a dialysis pumping system, and more specially to a single needle dialysis apparatus with a dialyser having blood and dialysate circuits and which has blood inlets and outlets that are joined by intake and outlet lines with at least one blood connection. The intake line has a driving pump and a blood pump powered by driving fluid from said driving pump and pump valves placed upstream and downstream from the said blood pump. Furthermore the outlet line has a further shut off valve. The blood pump unit has a generally stiff housing with a pipe-like liner in it walling off the space in the housing into a first chamber for blood and a second driving fluid chamber that is joined up with the driving pump, that may be a bellows pump and is joined up with the housing by an air circuit with sensors or valve driving parts for controlling motion of air into and out of the housing.

16 Claims, 10 Drawing Figures

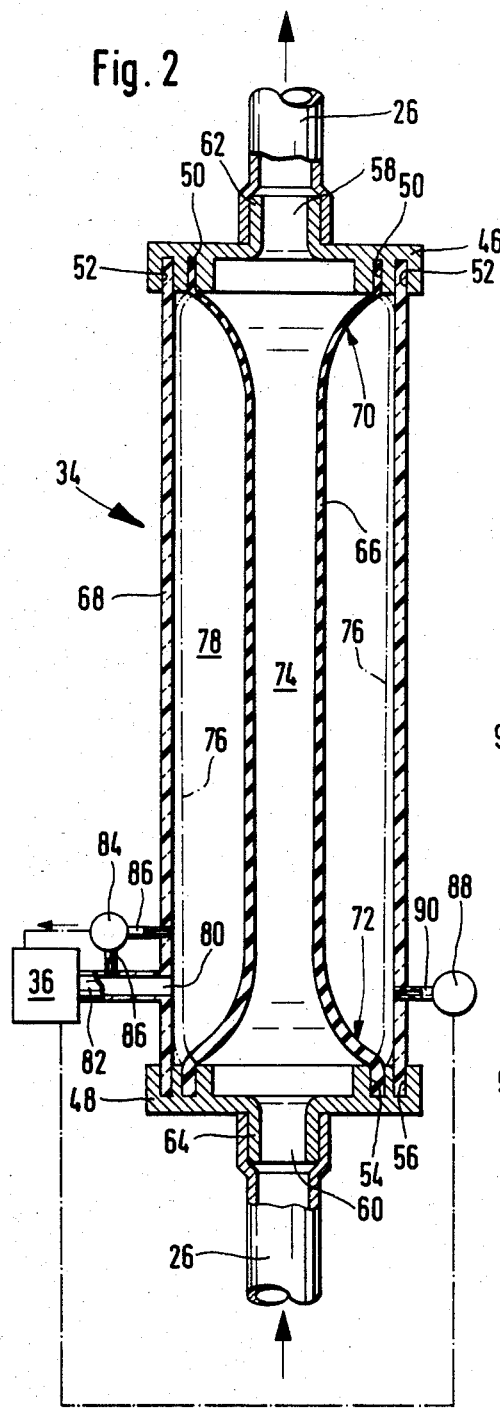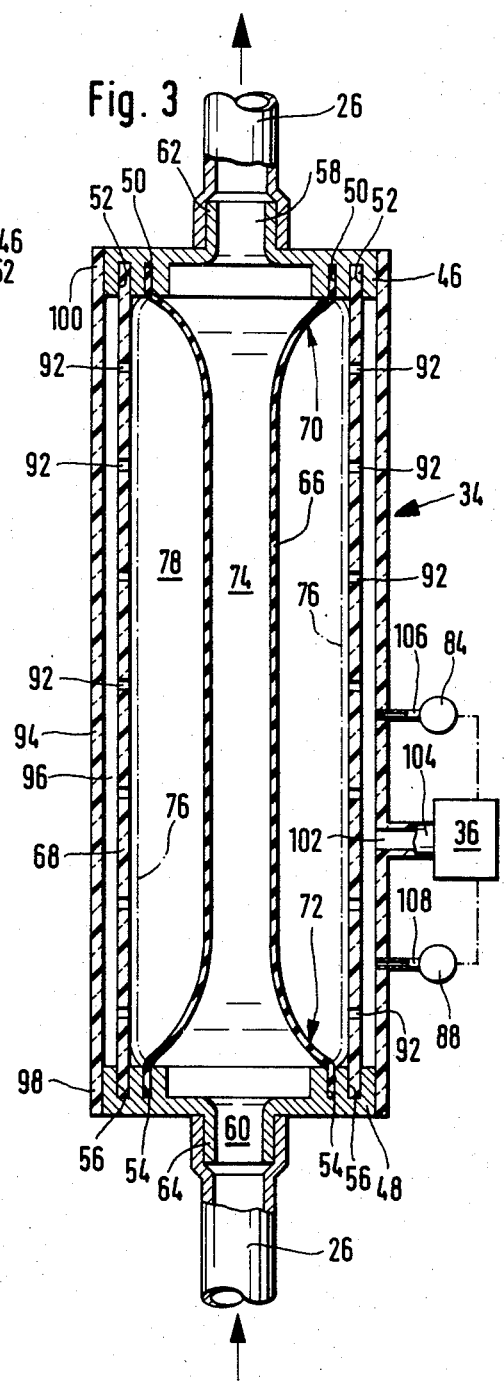

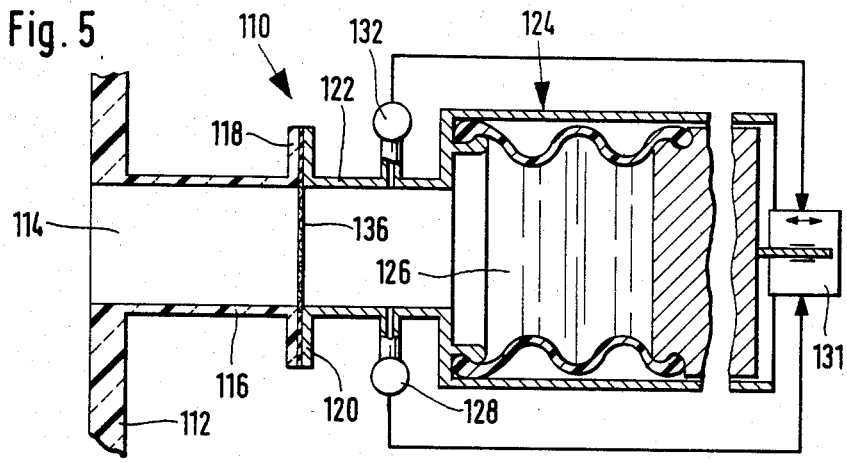
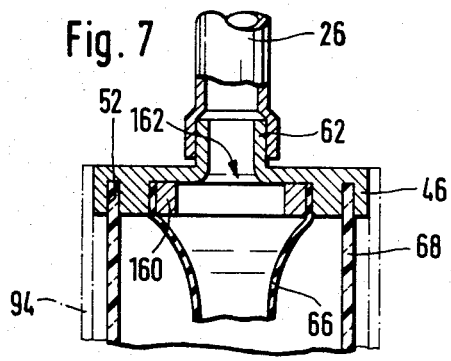
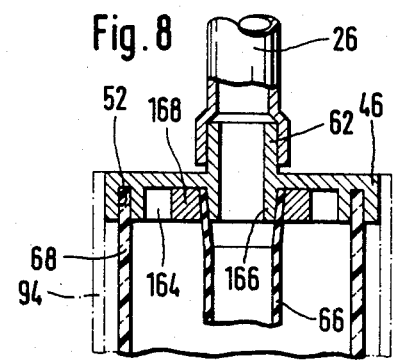
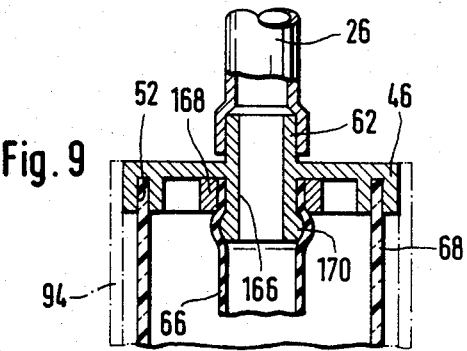

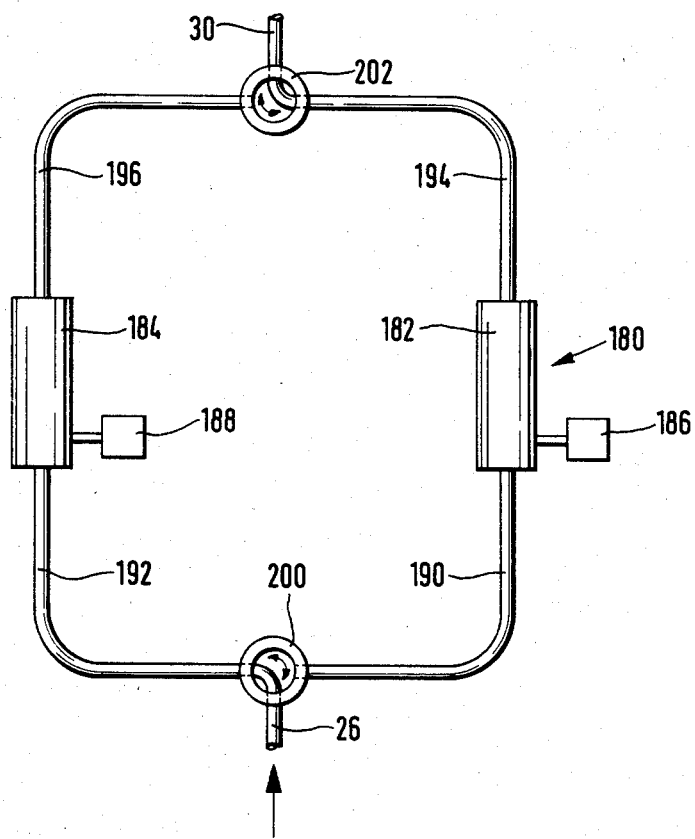

PUMP SYSTEM FOR USE WITH DIALYSIS AND LIKE APPARATUS

BACKGROUND OF THE INVENTION

The present invention is with respect to a dialysis pumping system for clearing products of metabolism from the blood of a patient, and more specially to a single needle dialysis apparatus with a dialyser having blood and dialysate circuits and which has blood inlets and outlets that are joined by intake and outlet lines with at least one blood connection. The intake line has a driving pump and a blood pump powered by driving fluid from said driving pump and pump valves placed upstream and downstream from the said blood pump. Furthermore the outlet line has a further shut off valve. The blood pump unit has a generally stiff housing with a diaphragm therein walling off the space in the housing into a first chamber for blood and a second driving fluid chamber that is joined up with the driving pump, that may be a bellows pump.

DISCUSSION OF THE PRIOR ART

An apparatus designed on these lines will be seen in the U.S. Pat. No. 3,791,767 to Schill, in which as part of a single needle dialysis system there is a special design of pump with which there is likely to be less damage to the blood than was the case with earlier known systems using peristaltic pumps. In fact in the said U.S. patent the blood is taken up into a hose-like, collapsible straight pump chamber at one valved end thereof and then forced out of it at the other valved end when, in the next pumping step, driving fluid is forced into the space round the hose or sleeve and the same collapsed thereby. To make such driving of the blood pump by the driving fluid possible, the flexible liner or sleeve is placed within a generally stiff casing so that there is a ring-like space between the two round the liner into which liquid may be forced by the driving pump and then let off again from the casing as one cycle of a pulsating pumping effect.

In the patent the driving pump for causing the pulsating operation of the liner has a piston joined up with a bellows that may be moved against the force of a spring by a solenoid, the space inside the bellows then increasing and liquid being taken up out of the ring-like space of the pulsating liner pump. Because of the vacuum effect in the liner or flexible tubing, blood is taken in till the liner has come up against the inner wall face of the casing, at which however its further expansion is stopped. The volume of blood taken up is in this case limited by the amount of liquid in the driving pump system and the volume within the liner. For pumping blood out of the liner again, the solenoid is turned off so that the bellows is acted on by the restoring force of the spring and is so forced together pumping the driving fluid back into the blood pump.

This constant-volume system does however have some serious shortcomings that are produced by the special form of blood pump with which it is designed.

In fact the possible adjustment of the degree of vacuum and of gage pressures acting on the blood is very limited and the acting levels of vacuum and gage pressure are more or less completely dependent on the design of the separate pump elements. The bellows, and for this reason the driving fluid, is pushed back because of the constant force of the spring, such pressure effect acting furthermore directly on the blood itself because the driving fluid is a liquid and so incompressible. This sort of adjustment-limiting effect would seem likely in connection with the solenoid as well so that one may take it that there is in fact no control of the pressure. This being the case, a relatively exact adjustment of the pump liquid would be needed to make the pump efficient.

While it is true that the driving liquid is pumped back, this is without there being any controllable vacuum effect in the pump system, seeing that the blood, if there is no resistance to flow, will come into the liner automatically because of its own pressure, the liner then coming out of its collapsed condition and opening out or swelling, even without there being any vacuum effect, into the expanded but still pressureless condition. A further shortcoming of this pump system is that at the start of the pumping operation the storage unit and the bellows pump have to be timed in the first place before regular operation of the pump system is possible. Such a timed condition is however not readily produced as a rule and, in the special case of the use of an incompressible fluid as the pump driving fluid, the storage chamber will not be completely filled up with blood. In view of the fact that there may be a change in the timing relation between the storage chamber on the one hand and the pump on the other hand even while the system is running, it is hard to make certain of regular operation of the pump.

It will be seen from these observations that the pumping effect of this pump system will not be quite in line with the desired pumping operation in the filling up stage or when the system has started running, because, but for the amount of driving liquid, no changes or adjustments may be made in the parts of the system or the way it is run.

A further earlier system has been put forward in the U.S. Pat. No. 3,811,800, again using a pump with a pulsating and automatically expanding liner whose degree of expansion is however limited. The pulsating liner is placed in a further flexible pipe or hose and the space therebetween is filled with a hydraulic driving fluid. When such driving fluid is forced into the outer hose it is expanded and at the same time the blood is forced out of the inner hose or liner, while on the other hand when the driving fluid is let off from the said space the liner is opened out and becomes filled with blood again, to which end clamp valves have to be worked to let the flow of blood take place.

From this it will be seen that the pumping effect is produced with a hydraulically driven pump that is housed in a stiff casing having a smaller overall volume than the volume of the two flexible hoses, so that one of the hoses is always in the act of collapsing. As will have been seen from the observations made so far herein, there are special shortcomings in connection with pressure control inasfar as there are no simple safety measures one may take for limiting the degree of compressing force. In point of fact, in a working design of such a system pressure limiting valve and complex filling programs with support components are needed to make this possible.

In this form of the system it is furthermore not possible for the blood aspiration speed to be controlled, seeing that it is in fact limited by the elastic memory of the blood pumping liner and restoring force of the hydraulic system joined up therewith. In other respects no regulation is possible.

The German Offenlegungsschrift specification No. 2,455,917, that is in connection with an external circuit and single needle system, has a blood pump with adjustment of the inner volume. As for the design of the blood pump, it may be in the form of a pump with a pulsating liner, noted earlier as having some undesired effects, or a pump with a pipe-like diaphragm and valves, that is to say controlled inlet and outlet valves. Such pumps are known as ventricle pumps because of their pumping the blood in one direction only.

It is in this case a question of an expansion vessel powered by a driving pump of which no details are given.

An account of such a bellows-like expansion vessel, that comes into contact with the blood itself, will furthermore be seen in Medizinal-Markt/Act Medicotechnica, 26 (1978), 12, pages 381 to 383. Such a mechanically driven bellows pump has the shortcoming of not itself limiting the degree of vacuum or gage pressure so that, to do this, here has to be a special pressue pick up as part of the blood inlet system for controlling the speed of driving the bellows into its collapsed or expanded condition.

In their relation to the present invention the only point that is to be kept in mind in connection with the prior art pump systems noted so far is that they have a constant volume positive control effect or they have a pressure control system joined to the blood pump. Furthermore regular, as-desired operation of such pumps is not possible if they are started up out of the timed condition and in fact a special filling program and supporting components are needed for this.

Further dialysis systems on these general lines are to be seen in the German Offenlegungsschrift specification Nos. 2,17,900 and 2,636,290 and furthermore in the British Medical Journal, vol. 281, (1980) page 1109, such systems however being based on the use of pulsating liner blood pumps with their noted shortcomings; for still further examples of such blood pumps working in much the same way, see the German Offenlegungsschrift specification Nos. 2,143,628 and 2,340,755.

OVERVIEW OF THE INVENTION

It will have been seen from the account so far that one purpose of the invention is designing a system of the sort noted with which one may be certain of the pump filling and emptying whatever the conditions of operation, as for example in the starting up stage or thereafter.

A still further object or purpose of the invention is the design of such a system making possible such operation without a pressure pick up or sensor joined with the blood pump or the blood intake system for automatic control of the blood pump.

For effecting this purpose and further purposes the driving pump is a bellows pump with sensors or valves for controlling it in respect to the degree of gage pressure or of vacuum.

In the first place one useful effect of the system in keeping with the invention is that the driving pump is controlled or controlled automatically without being dependent on a separate controller or automatic controller joined with the blood pump pump, the last-named in fact automatically controlling itself as from a certain level of gage pressure or vacuum in the blood pump, whereafter the valves are opened for stopping any further increase or decrease, whichever may be necessary, in the fluid driving the blood pump.

Such a design may hardly be based on the use of a hydraulic pump as noted hereinbefore, because liquids, that is to say incompressible fluids, are regularly used in pump systems working with a constant volume so that, as one may see, the driving pump and blood pump may only be positively controlled.

In the system in keeping with the present invention however, in which operation is pneumatic, adjustment may be undertaken to any desired degree of gage or vacuum pressure without any fear of damaging the blood pump, this being because the compressible nature of the air used makes regulation very much simpler.

One specially useful effect produced by the invention is that there is not the least trouble with priming the system at the start of dialysis; it is not dependent on the timing relation, and in fact blood is aspirated into the pump chamber till the elastic diaphragm is resting against the stiff or rigid casing of the blood pump and for this reason the pressure does down. It is for this reason that the vacuum valve is opened and keeps the degree of vacuum at an unchanging level till vacuum is again produced by the pump.

At the reversal point of the pump, the blood pump is emptied till the liner or hose-like diaphragm is completely collapsed, this making the pressure go up. At this point the gage pressure valve is opened. However the pump goes on functioning and at its lower dead center or reversal point is changed over to aspiration operation. At this point it will be correctly timed. It will be seen from this that only one cycle is needed by the pump to get into the timed condition.

In a more specially preferred form of the invention the inside volume of the blood pump and of the bellows or driving pump is correlated so that the ratio between these two volumes is limited. It is for this reason that the pressure as well has its own limit in this pneumatic system so that in some cases it is possible for the system to go on working even after the control valves have stopped functioning.

In keeping with the invention the wall of the blood pump is able to be elastically stretched so that the overall volume of the pump may be increased many times over. Because of such elastic expansion a pressure comes into being acting on the blood taken up in the pump, such pressure being dependent on the volume of such blood. The pump itself has as its main part a generally stiff or rigid body that is best made in the form of a hollow cylinder, and as a further part a pump or storage body placed coaxially in the hollow cylinder and best made in the form of a piece of hose or flexible liner. Between the liner and the stiff body there is a ring-like or annular space to let expansion of the liner used as a pump element take place, the overall volume of the blood pump being dependent on the inner volume of the hollow cylinder.

In view of the fact that forces are needed for causing expansion of the blood pump the rigid body has a port with a connection for the input and letting off of driving fluid from and to a driving pump. This fluid, which is preferably air, takes effect all over the outer face of the liner, the same swelling out, if there a vacuum, till it has taken up all the inner volume of the hollow cylinder, while when there is no longer any vacuum it will go back into its starting position because of its elastic memory pumping out the blood.

This pumping of the blood naturally only goes on till the liner is back in its starting position, although it is possible for it to be moved past this point by forcing further driving fluid into the liner. On doing this, all the blood may be forced out of the liner or pump diaphragm.

The pressure characteristic is naturally a function of the length and the cross section of the liner and more specially of its wall thickness. Generally the liner with the desired size will be able to take up twenty times and more of its volume it has in the starting position without there there being a sharp upward turn in the pressure curve. The pressure characteristic or function will have such a form that after filling up of the liner under pressureless conditions there will be sharp upward turn in the curve as further blood comes into the liner and there will then in the end be a leveling off to a part of the curve that has a small upward slope or is even a plateau, this being at a twentyfold volume increase. However any further increase, even only a small one, in the blood taken in will then be the cause of a sharp increase in the pressure. Such a liner or storage vessel may be on the one hand be readily monitored—this being because only a small change in pressure is all that is needed to go past the upper or lower pressure limit—and for this reason pressure control is made very much simpler. This being so, control of the mean pressure as used in other single needle apparatus is not needed. Furthermore in the pressure plateau range the output of blood will be generally in the same pressure range so that the pressure at the dialysis membrane will be more or less constant and no trouble conditions are to be feared in the dialysis process itself.

Because the blood is taken up into and stored in the pump liner by causing expansion thereof in an outward direction by the use of vacuum, there is no mechanical wear of the liner or pressure storing element and so no chance of such materials making their way into the body of the patient. Furthermore the blood is forced out of the expanded liner because of its elastic memory automatically and it is only necessary for the liner or pump element to be acted upon by vacuum using the driving pump. More specially, there is one useful effect here inasfar as the blood is let off out of the liner at a generally constant pressure, this being because of the more or less level plateau of the pressure function curve.

Because the starting volume of the pump element becomes very much greater as it becomes filled with blood, control of the system by sensing the changes in volume would be possible as well using optical or mechanical sensing elements. It is naturally furthermore possible for the pump element to be run without elements for sensing the pressure or the degree of filling, if for example a pump with a constant pumping volume or displacement were used. Then it would be possible for the displacement to be equal to or less than the volume of the blood pump or store volume. On the other hand this displacement may be controlled by pressure limiting elements, as for example in the form of vacuum and gage pressure valves, inasfar as the displacement of the pump is greater than the store or buffer volume of the blood pump. This being the case, it will then be possible, in combination with such a fixed-function pump to do without a pressure or volume control system.

The liner or pump element in keeping with the present invention has the nature of a mass-produced article, that is best manufactured from commercial quality rubber hose material and for this reason may be simply made without any troubles on the technical side. It may be readily sterilized and may be produced and marketed alongside other parts of the dialysis apparatus.

Further details and useful effects of the invention will be seen from the account now to be given of working examples thereof to be seen in the figures herein.

LIST OF VIEWS OF THE FIGURES

FIG. 2 is a lengthways section through a first working example of the pump vessel.

FIG. 3 is a lengthways section through a second working example of the pump vessel in keeping with the present invention.

FIG. 5 is a view of a diaphragm pump vessel for use as part of the pump to be seen in FIG. 1.

FIGS. 7 to 9 are lengthways sections through end parts of further vessels of the invention with a rough view of the cylindrical outer wall of the vessel.

FIG. 10 is schematic of a continuous pumping system having two pumping vessels.

DETAILED ACCOUNT OF WORKING EXAMPLES OF THE INVENTION

Figure 1:
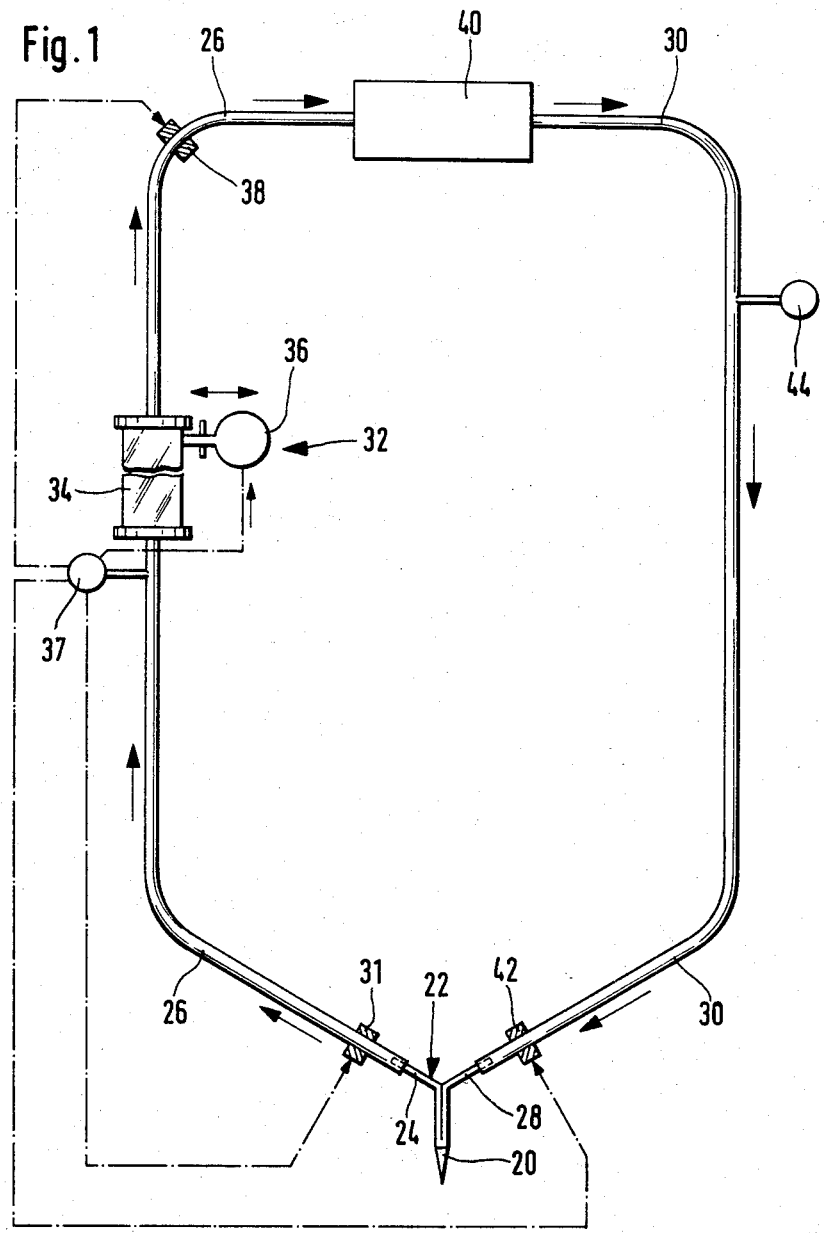
FIG. 1 is a diagrammatic and general view of a single needle dialysis system with the pump system in keeping with the present invention.

In FIG. 1 the reader will see a dialysis system taking blood from a patient by way of a hollow needle 20, that is pushed into a blood vessel. This hollow needle 20 has a Y-like two-armed connector 22 at its one end, of which the one arm 24 is joined up with the artery line 26, whereas the other arm 28 is joined up with a vein line 30 or duct. The hollow needle 20 may be in the form of a biflow needle, that is to say a needle made up of two needle parts placed coaxially one inside the other so that one needle part of the needle structure comes to an end some millimeters short of the end of the other needle part for stopping any mixing effect. On the other hand a certain degree of mixing may be put up with at the Y-like needle 20 that is preferably used in the invention.

At a point along the artery line at some distance from the hollow needle there is a clamp 31, with whose help the artery line 26 may be shut off. Further along the artery line 26 there is a pump system 32 that is joined up with the artery line 26 and whose main parts are the pump vessel 34 and the driving pump part 36 joind up therewith. Downstream from the pump system 32 there is then a further shut off valve 38 that is best in the form of a clamp or, however, in the form of a check valve.

Downstream from the shut off valve 38 the artery line 26 is then joined with the dialyser 40, in which the blood to be cleaned is freed of the products of metabolism and excess liquid. This dialyser 40 is joined up with a dialysing system (not made part of the figure) for pumping the dialysate through dialyser 40 by way of inlet and outlet lines, not viewed in the present figure.

The outlet part of the dialyser 40 is joined with the vein line 30 whose other end is fixed on the other arm 28 of the Y-like hollow needle 20, after running through a further clamp 42, with which the vein line 30 may be shut off and opened up.

Furthermore a useful effect may be had by placing a pressure pick up or sensor element 44 on the vein line 30 for getting a reading for the pressure building up at a point between the shut off valve 38 and the clamp 42 in this part of the line 30.

An account will now be given of the operation of the first working example of the invention.

The patient's blood is taken up by way of the hollow needle 20 into the pump system 32 of which a more detailed account will be given hereinafter in connection with FIG. 5, the shut off valve 38 and the clamp 42 being in the shut position and the clamp 31 being opened. By way of the artery line 26 the blood is pumped into the pump vessel 34 by the operation of the pump part 36, the said pump vessel 34 in the form of a pipe-like liner (of which the reader will be given a more detailed account hereinafter using FIG. 2) firstly being filled up with blood without using vacuum. Nextly however expansion of the wall of the said vessel or liner is started so that there is a quick or sharp change from the pressureless condition to one in which the blood has to be acted upon by vacuum necessary to overcome the changeover from the collapsed condition of the liner in the vessel to one in which its wall is pulled tight, this being somewhat like events on blowing up a balloon. The function or pressure characteristic in a liner 66 (see account below) of the vessel 34 on testing with pressure therein will be seen in FIG. 4.

A useful effect may be produced in the first example of the present invention by having a pressure pick up 37 or sensor in the artery line 26 having the function of turning off the pump part 36, or steplessly cutting back its pumping rate when the pressure in the line 26 goes outside certain limits: in fact if the pumping rate through the artery line gets as far as a value that is equal to the flow in the shunt there will be vacuum in the vein shunt itself and this will be responsible for the needle coming up against the wall and the system getting out of order. In such a case, no more blood will be pumped and there will be heavy hemolysis. Such a pick up 37, acting through a controller (not figured), may have such an effect on the pump part 36 that its rate is cut back steplessly (so that, for example, adjustment of the maximum blood flow in the external blood circuit may be made) or the pump itself may be shut down.

The same events will take place when the pressure becomes greater than a maximum gage pressure limit, as when the line of the dialyser becomes stopped up. In such a case the pump part 36 is turned off by the pick up 37.

In FIG. 2 the reader will see the first working example of the present invention in the form of a lengthways section through the pump vessel 34. This pump vessel 34 has more or less round end plates 46 and 48, having round grooves 50, 52, 54, and 56 molded into them. The two end plates 46 and 48 each furthermore have a port 58 and 60 within connectors 62 and 64. It is on these connectors 62 and 64 that the two lengths of the line 26 are slipped and elastically kept in place or are fixed by adhesive.

The two end plates 46 and 48 are joined fluidwise and mechanically together by way of the expanding liner 66 or flexible hose and the hollow-cylindrical casing 68. The liner 66 is elastically stretched outwards at its ends 70 and 72, that is to say pulled outwards in a diametral direction and furthermore the rims or edges of such ends are let into the ring-like grooves 50 and 54 of the said end plates 46 and 48, in which they are fixed. However in its middle part between its ends the liner is not stretched in the diametral or crossways direction but only, as a useful further development of the invention, pulled out elastically or pre-stretched in the direction of its length. The said casing 68 or pump vessel is fixed and locked at its ends in the ring grooves 52 and 54 of the end plates 46 and 48, such fixing in position being for example by the use of an adhesive or by a force fit.

As may further be seen from FIG. 2, the inside space 74 of the liner 66 is joined up with the port 58 and for this reason with the artery line 26 and when the pump is working it is filled with blood. The effect of such blood is that there will be expansion or swelling of the wall of the liner 66 till it is fully resting against the inside face of the casing 68, as is marked by the broken line 76.

For producing such an elastic swelling or expansion of the liner 66, it is naturally necessary for the outer face of the liner 66 to be acted upon by a vacuum in the generally ring-like space 78 formed between the liner 66 and the inner face of the casing 68 and for this purpose there is at least one port 80 joined up by way of a line 82 with the driving pump part 36 of the pump system 32. For more details of this pump, see FIG. 5 and the account thereof. By way of line 82 and port 80 a fluid, that is more specially air, is pumped in and out of the ring-like or annular space 78 for causing expansion and collapse of the liner 66, whichever is needed at a given time.

Because of the highly elastic properties of the liner 66 and the way it is supported and kept in position (see FIG. 2), collapse of the liner 66 is not complete without help and in fact for completely pumping the blood out of the inner space 74 a certain gage pressure is needed in addition, such pressure being produced by the pump part 36 of the pump system 32.

In order for blood to be taken up into the liner 66 a degree of vacuum of about 150 mm Hg (the maximum being 500 mm Hg) is needed, such vacuum level being controlled by way of the pick up 37 or preferably the sensor 84, that is joined up with the ring-like space 78 and/or the line 82 by way of the line 86. This pick up 84, that may be adjusted to any desired pressure value for operation of the pump system 32, is more specially used for automatic control of the vacuum, whereas a further pick up 88, that is joined up with the ring-like space 78 as well through a port and the line 90, is used for controlling the pressure that is to be produced in the ring-like space 78 for causing full collapse of the liner 66, this pressure naturally being dependent on the degree to which the liner 66 is (pre-)stretched (by the pulling forces acting thereon in its resting condition) within the pump vessel 34 and on the viscosity of the blood in the liner 66.

For control of the pump part 36, the two pressure pick ups 84 and 88 are naturally joined up therewith.

The liner 66 may be made from any one of a number of highly elastic materials, examples of these being organic polymers and blends or mixtures thereof, such as polyurethanes, rubbers, silicone rubbers, latex, vulcanized rubbers, regenerated rubber and the like, latex material however being with or without normal additives for increasing its elasticity. Expansion of such a liner 66 may be such that its lumen is increased five-fold, or, better still, ten-fold, that is to say that it will take up a volume of blood—at least in the preferred form of the invention—equal to ten times its inner volume in addition thereto.

The wall thickness of such a liner 66 or hose will be in a range of roughly 0.05 to 0.5 mm and more specially 0.1 to 0.4 mm, the figure for this being dependent on the desired pressure function and the increase in volume of the pump vessel 34 that is to be used. The thicker the wall of the liner 66, the higher will be the starting vacuum necessary for getting onto the pressure plateau stretching over a wide volume range as noted earlier herein. It is best for the selection of the wall thickness to be such that the pressure plateau is higher up than the pressure in the vein and is preferably greater than 20 mm Hg. Putting it differently, there has to be this pressure in the vein line before any blood may be run into the vein.

The volume of the liner 66 and the length thereof will be dependent on the purpose of use and the design of the dialysis apparatus. Normally the diameter of a liner 66 will be within a range of 5 to 15 mm and will more specially be equal to 8 mm, whereas the length of the liner 66 may be preferably 15 cm and more generally within a range of 10 to 20 cm. However it is still possible to have shorter or longer sizes of liner if the use of the pump apparatus makes this necessary. If only small blood volumes are to be pumped, the pump vessel will be representatively smaller in size than when it is a question of pumping high rates of blood.

In the first working example of the invention to be seen in FIG. 2 the liner 66 has a wall thickness decreasing from the one end plate 48 to the other end plate 46, such decrease preferably being, as measured along the full length of the pump vessel 34, by up to 50%. Such a liner 66 having a generally unchanging or regular rate of decrease in wall thickness along its full length may be manufactured by dipping a rod into a mass of liquid latex and then afterwards pulling out of the said liquid latex compound. Because of the liquid condition of the said latex compound there will be a motion thereof in a downward direction of the rod with the outcome that the liner or sleeve formed thereon will have an increase in the wall thickness in a downward direction from one end thereof to the other. This being so, the pressure function after a sharp upward turn or increase at the start of blowing up or inflation of the liner 66 (see FIG. 4) will go into a flat part with an unchanging upward slope.

This design and placing of a liner 66 to be seen in FIG. 2 is important for the selection of the position of the port 80 joining the liner 66 with the pump part 36 by way of the line 82, this port 80 in fact being near the liner end 72 where it has its greatest wall thickness. In fact the swelling of the liner 66 will be started at first where the wall is thinnest, that is to say, near the end plate 46. When such swelling takes place, the first sign will be that the end part of the liner is moved outwards and up against the inner face of the casing 68, such expansion then moving along the length of the liner 66 as a sort of wave front towards the end of the liner with the greater wall thickness.

In FIG. 3 a further working example of the invention will be seen in which parts which are the same as the parts used in the example of FIG. 2 have the same part numbers. In the example of FIG. 3 there is as well a liner 66 or hose, whose wall thickness is however this time generally the same right the way along its length. However this form of the invention is not to be limited to the use of such a liner with a generally even wall thickness and in fact liners with a wall thickness that becomes less in the direction of the length as was the case with FIG. 2 may be used.

This working example of the present invention of FIG. 3 is mainly different to the structure of FIG. 2 inasfar as the casing 68 has a number of ports 92 with any desired distribution along the length of the casing and in the direction round its axis. It is by way of these openings or ports that the fluid, that is taken up by the pump part 36 or pumped out of it, may make its way in and out of the casing.

As a further change this second form of the invention has a further outer wall 94, whose diameter is greater than the diameter of the casing but otherwise generally is of the same geometrical form as the casing 68 or vessel wall. Given a cylindrical form of the two walls, there will be a ring-like space 96 between the two, this space being joined up by way of the ports 92 with the ring-like space 78. The outer wall 94 has its end parts 98 and 100 locked in and joined up with the end plates 46 and 48. But for the port 102 in the outer wall 94 the structure may be looked upon as being generally airtight and having its inside spaces shut off from the outside. The port 102 may be placed at any point on the outer wall 94, seeing that the liner 66 may only be opened out as far as the vessel wall or casing 68 and because of the large number of ports 92 one may be certain that the liner 66 or hose will not have the effect of a stopper shutting off the fluid outlet port, something that would then make it impossible for any further fluid to be pumped out of the pump vessel 34.

Such a form of the invention is more specially of value when the liner 66 has an unchanging wall thickness all over, because, as a general rule in this case swelling out of the liner as it becomes filled up with blood will not take place starting at one end and moving along to the other in the form of wave as was the case with FIG. 2. In fact, swelling of the liner 66 may be started at any point along it. The design in this case will make certain that there will be an even filling of the liner 66 till it comes to rest against the inner face of the vessel wall 68, possibly along its full length.

The port 102 is for its part joined up with the pump part 36 by way of a line 104. Moreover, as in the case of the first form of the invention there are the two pick ups 84 and 88 or sensors, that by way of lines 106 and 108 ports therefor in the outer wall 94 are joined up with the ring-like space 96.

It is best for the size selection of the liner 66 to be such that the space 74 be about 50 to 80 ml in volume, while in the pressureless condition the volume of the liner 66 is about 10 to 15 ml.

A further point to be kept in mind is that the material for the elastic liner 66 may be may be any waterproof material that has a high enough ultimate elongation (over 200%), all the materials noted hereinbefore having such properties.

The pump vessel wall or casing 68 and the outer wall 94 are to be made of stiff materials, as for example polymers selected from the group polyethylene, acrylic glass, PVC and others.

The fluid in the ring spaces 78 and 96 will generally be air, although however liquids such as water or the like may be used in place thereof.

When, on running the working examples of the invention blood is taken up into the liner 66 by producing a vacuum with the pump part 36, there will in the first place be only a small increase in vacuum seeing that the liner 66 will become filled with a small degree of swelling and only a small increase in volume. Thereafter further swelling of the liner 66 will be limited to a point of the liner 66 where its wall is least strong or thinnest, such swelling so taking place that the liner 66 comes up against the vessel wall or casing 68 more and more or progressively till the space 78 is completely cleared of fluid and in fact is completely taken up by the liner 66. This second form of the invention is different to the first one inasfar as in the first case, because of the decrease in the wall thickness of the liner 66 along its length, swelling of the liner 66 will take place in a wave or wave front sweeping along the outer casing from one end to the other axially and the vacuum needed for producing such an effect will generally keep at the same level, whereas in the second form of the invention there will be a smooth change or continuous progression in the vacuum or negative pressure causing the swelling of the liner 66 whose wall is generally equally thick from one end to the other.

Once the fluid has been completely pumped off from the space 78 so that the lining hose 66 is resting along the pump vessel wall as marked by line 76, there will be a sharp increase in the pressure because the liner is now not able to give way and be deformed any more.

Once the pressure level has got up to the upper limit to which the pick up 84 has been adjusted, the vacuum pumping effect of the pump part 36 is turned off and a shut off valve (of which an account will be given in connection with FIG. 5) is opened in the pump part 36, this letting in fluid into the space round the liner 66 which is now able to go back into its starting position. On operation of the pump it goes without saying that the clamps 31 and 42 as well as the shut off valve 38 are worked with the timing needed to give a pumping effect. If, in a given case, the liner 66 is acted upon by fluid because of the operation of the pump part 36, then at a given gage pressure level, that is to say when the liner 66 has been completely squeezed together and screwed up, the pick up 88 will be tripped and a new cycle may be started.

Figure 4:
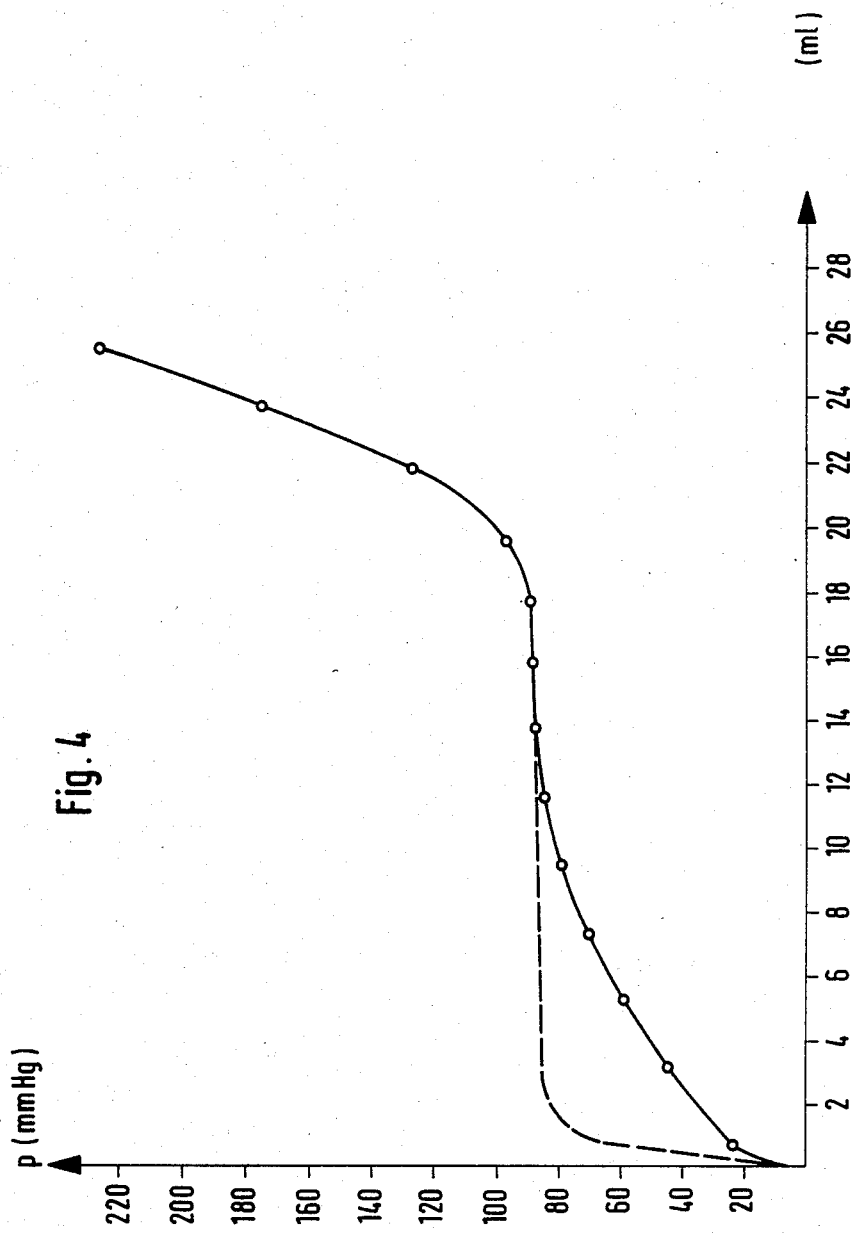
FIG. 4 is graph of the volume pressure function of the form of the invention seen in FIG. 2 at the time of filling the pump vessel.

In FIG. 4 the reader will see the pressure-function produced on testing under pressure an example of the first form of pump vessel as marked by a full line while the ideal function of a pump vessel with an even wall thickness is marked in a broken line. The graph is naturally with respect to the blood volume running into a liner 66 that has first been filled up at normal pressure. As noted earlier herein the form of liner 66 used in the first working example of the invention may be manufactured by a dipping process in which a rod is dipped into a latex bath and is then slowly pulled upwards out of it again, this being in line with the smooth or straight upward slope of the pressure-blood volume function as blood is taken up in the liner.

Seeing that there are pressure and volume changes in the elastic liner 66, readings with respect to pressure or to volume may be separately of equal value in a system for control of the pump vessel 34, or pressure and volume readings may be used at the same time for this purpose.

In FIG. 5 a special form of pump part 36 is shown as pump part 110. It 110 will be seen, that may be used as part of the pump system 32 in the first or in the second forms of the present invention. In this case the wall 112, having the same function as the casing 68 or the outer wall 94, has a port 114 running through it and into the ring space 78 or 96, whichever is the case, on the inner side of the wall 112. On the outer side of the wall 112 the port 114 is joined up with the line 116, that is the same in function as the line 82 or 104.

At its other end the line 116 or pipe has an adapter 118, as for example in the form of a flange or a luer-lok adapter, for joining with a further adapter part 120 to give a gas-tight connection therebetween. The further or right adapter part is joined up with a line 122, that for its part is joined to the bellows pump 124.

It is to be noted that herein the wording bellows pump is used in respect of a pump with a constant displacement or stroke volume. The bellows pump 124 is best one whose displacement is greater than the take-up or storage volume of the pump vessel 34, the more specially preferred form of pump 124 being one in whose volume is up to 20% greater than the volume of the pump vessel 34.

Using this bellows pump 124 the fluid is taken up from the inner part of the pump vessel into the bellows 126.

In this pressure controlled form of the invention the pump is switched over at certain upper and lower pressure limits or pressure values within the line 122. Other designs of pump may be used in place of a bellows pump. This control is so undertaken that (a) the pump is turned off when the pump vessel 34 is full (in which case by way of an air inlet valve, not figured, air may make its way into the line 122 and the elastic pump vessel 34 may go into its starting condition pumping out blood as it does so) or (b) the pump 124 may be switched over to pumping (in place of aspiration) in air through the line 122 into the ring space 78 so that the pump vessel will be decreased in volume.

For fixing a given limit for the degree of vacuum in the pump system, and more specially within the line 122 there is a pick up 84 therein for switching over operation of the pump part at a given vacuum adjustment as fixed beforehand. At the same time the clamps 31, 38 and 42 are switched over.

In the case of positive control, with the pump part functioning in a cycle between upper and lower dead center positions or points of reversal, that is to say upper and lower pressure limits, these pick ups are not fully necessary and in fact if a bellows pump 124 is used having a constant pumping volume and a constant pumping rate as fixed by adjustment in the first place, it is then possible simply to have a vacuum valve 128 in the line 122, such valve opening automatically when the pressure gets to a certain level of vacuum in this line. Preferably the adjustment of this vacuum valve will be so undertaken in the first place that the valve is tripped on the liner 66 becoming full of blood and coming to rest against the inner face of the casing wall 68. The pumping function of the bellows pump 124 will be automatically switched over at the dead center position or reversal point, and at the same time will be responsible for switching over the clamps 31, 38 and 42.

The next step will be the pumping off of the blood out of the liner 66 by way of the bellows pump 124 or by letting air into the line 122 using a valve that is not figured here, the liner then pushing out the blood in it because of its elastic properties.

Once the liner 66 is fully compressed, there will be a jump in pressure in the outer space if the bellows 126 goes on compressing, something that will be the case if the displacement of the bellows 126 is greater than the blood volume of the pump vessel 34. In this case it is best to have a valve 132 letting off fluid at an upper pressure limit from the line 122, in which the valve is placed so that the excess air is let off and one does not go above a certain pressure limit in the system. At the lower dead center position of the bellows pump 124 the clamp 38 and the vein line clamp 42 are shut and the artery clamp 31 is opened.

It goes without saying that one may do without the valves 128 and 132 if the bellows pump 124 used has a displacement that at the most is the same as the blood storing volume of the pump vessel 34. However such a design is not preferred because of its being likely to be technically less safe.

It will be seen from the observations made so far that there is no need for a pick up or sensor for switching over the pump. In this case if operation becomes irregular, that is to say if a clamp is not functioning or if the lines become stopped up, it will not be possible for there to be a blood pressure in the system that is greater than the maximum controlling the pumping effect. Because the pump 124—if its displacement is greater than the filling volume of the pump vessel 34—will always be functioning with an excess of air, the complete filling volume of the expansion space will be pumped even if there is a leak in the pump line 122 running between the bellows 126 and the expansion space 78. It is in this way that one may be certain of having a pump volume that is equal to the filling volume of the pump vessel 34 for each stroke. On counting the number of pump strokes (by using a counter that is not figured) it is possible for the throughput to be worked out directly by multiplication and to be displayed and by working out the differential coefficient with respect to time the pumping rate may be displayed.

In connection with the apparatus in general a useful effect, at least, is to be had if there is a way of sensing an interruption, as for example a stoppage of a line or a line coming off its connector, at any point. Such an interruption may be detected by measuring the pressures in the vein and artery lines using the pressure pick up 37 or 44. In fact this pressure will be changing because of the flow resistance in the line 26 or 30 and the needle 20 as the blood is pumped through them. These pressure pick ups 37 and 44 will be joined up with a monitoring unit (not figured) for switching off all of the apparatus when pressure values outside certain limits are sensed.

A monitoring unit 131 for functioning on these lines may however be used with the pump system of FIG. 5 as well. This monitoring unit is joined up with the valves 128 and 132 and furthermore with the pump 124, the monitoring unit taking the place of a unit (not figured) for displaying the opening of the valves 128 and 132. If, to take an example, the one of the lines 26 and 30 becomes stopped up, the expansion space 78 will only be filled with a limited volume of blood (the blood naturally being within the flexible liner), such space then behaving as if it were incompressible inasfar as the blood may not be run into it or be let off from it because of the stoppage. It is for this reason that the vacuum and gage pressure valves 128 and 132 will then not be opened after a part of the stroke of the bellows 126 has taken place or a fixed time after the time of switching over, but very much earlier. In such a case the apparatus will be switched off by the monitoring unit 131.

It is furthermore possible for such a monitoring unit 131 to be used as well for the automatic control of the pressure in the flexible liner 66 and the lines 26 and 30. This pressure is correlated with the pressure at the sensors 84 and 88 so that in a further preferred working example of the invention the connection of the monitoring unit 131 with the sensors 84 and 88 makes possible a stepless control of the pumping rate or speed of the bellows pump 124. This being so, it now becomes possible for the pressure produced in the lines 26 and 30 and furthermore in the liner 66 to be increased or cut back.

In keeping with a further possible form of the invention the pressure sensors or pick ups 37 and 44 may be united as single pressure pick up that will then best be placed near the Y-like connector 22 between the clamps 31 and 42. This pick up may for its part be joined with the monitoring unit 131 so that in the aspiration phase a reading may be taken for the degree of vacuum or negative pressure caused thereby and such reading used for control of the pumping rate and, on the other hand, taking a reading for the gage pressure in the pressure stage and using such reading for adjustment of the rate of pumping back blood.

The system noted so far may furthermore be used for automatic control of the pumping rate: if the flow rate through the shunt or the needle 20 is not large enough in relation to the pumping rate that it has been adjusted for, there will be some vacuum on expansion of the bellows 126, the level of such vacuum being very much greater than the value which is characteristic for the combination of the flexible pipe system and the needle. This value may nevertheless be detected, even if there is a vacuum pressure valve 128, from the time at which this valve is opened. A useful effect is to be had (doing without detecting this condition completely) if the gage pressure valve of the switch-over sensor is adjusted to a value, that is worked out by calculation from the data of the flexible pipe system or by testing. If the flow rate of the shunt great enough, the vacuum level will only become greater than this value, when the expansion space 78 is completely taken up. If this is not the case, the vacuum will become greater than this value earlier, the vacuum valve 128 being opened and the pump volume and pumping rate being limited thereby. The outcome is a pumping system that, while being made up of simple components, is technically safe with the pumping rate fully matched to the flow rate of the shunt. In this case the bellows pump 124 will be run at a high speed without seeing that the expansion space 78 becomes completely filled, but without, be it noted, any chance of taking a reading for amount of blood pumped on the footing of the number of pump strokes.

A further point still to be noted is that the placing of a pressure pick up in the blood line is much more critical than in the pump system itself. The pressure pick up 123 may be permanently joined up with the pump line 122, so that then the danger of leaks is completely unimportant. Another point is that the pick up may be acted on by the outside air without the danger of contamination having to be feared, and naturally an uncovered sensor or pick up may be used. This is made clear in FIG. 5, in which the pressure pick up 123 is joined up, in keeping with a preferred from of the invention, with the monitoring unit 131, the valves 128 and 132 not having to be joined up with the monitoring unit 131.

To make certain that, in the event of the liner 66 bursting, it will not be possible for blood to make its way into the pump part 36, in a preferred from of the invention each line branching off from casing 68 and 94 has a diaphragm with hydrophobic properties, marked at 136 in FIG. 5. Such a diaphragm that has been made or is hydrophobic in its properties may be made of PTFE and have thickness of 10 to 50 microns and a pore diameter under 1 micron, such a diaphragm keeping back the blood (at the blood pressures possible in the system) from moving out of the pump vessel 34, but lets through the air quite freely.

Figure 6:
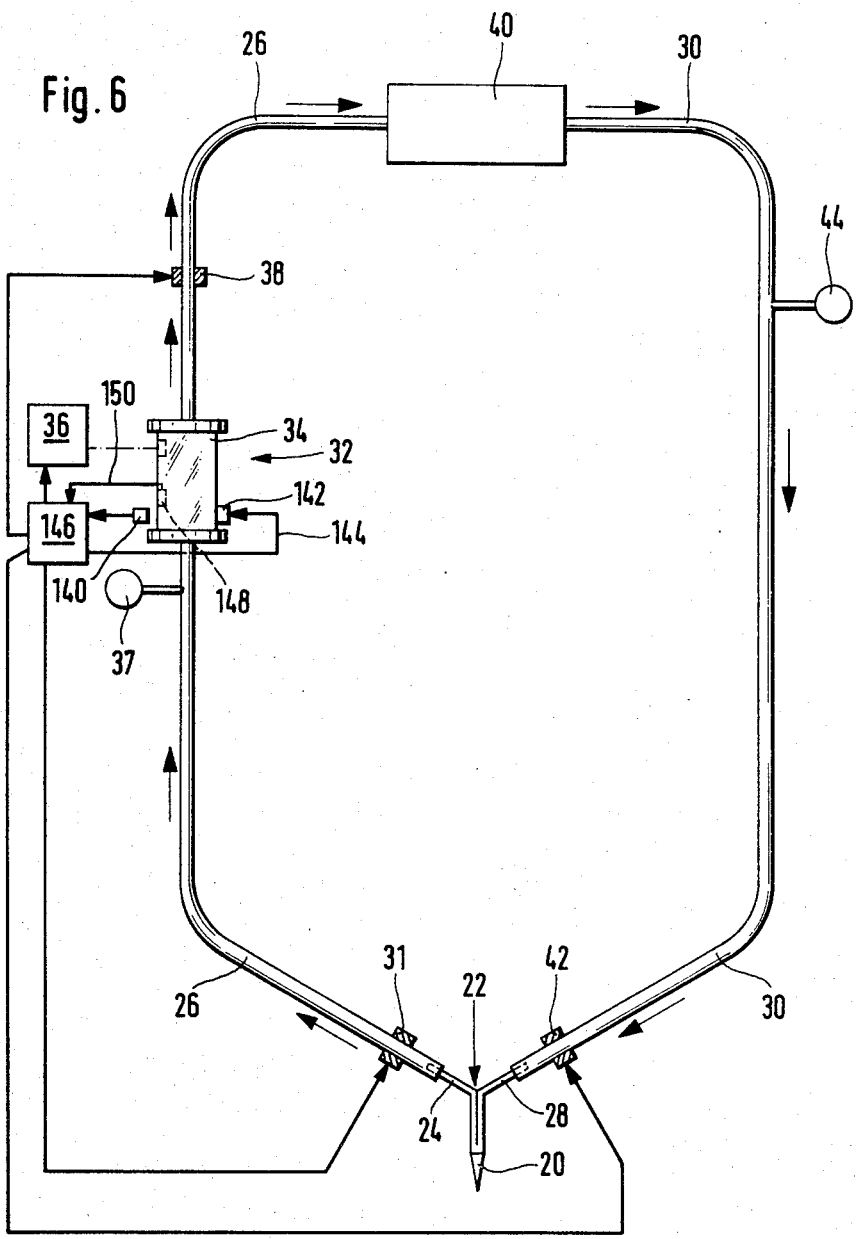
FIG. 6 is a further general and diagrammatic view of an apparatus with pump vessels in keeping with the invention in lengthways sections

In FIG. 6 the reader will see a special further development of the block schematic of FIG. 1, in which respect like parts are marked with like part numbers. Whereas in the system of FIG. 1 there was pressure control by the pump system of the present invention, in the form of the invention of FIG. 6 there is volume control. Such volume-based control is by way of a photoelectric (optical) pick up 140 placed at the outer face of the pump vessel 34 and joined by a wire 144 with a controller 146, the last-named controlling the pump part 36, the clamps 31 and 42 and furthermore the shut off valve 38. This controller 146 may on the other hand have a connection with the pick ups 84 and 88 as well. The photoelectric pick up 140 and its light source 142 are placed at and in relation to the outer face of the liner 66 so that the light from the source 142 is directed through the space 78 and in the form of a beam takes effect on the pick up 140 that is sensitive to such light. If the beam is cut off by the expansion of the liner 66, a signal will be sent to the controller 146, the same then turning off the pump part 36 and shutting the clamp 31 while on the other hand the shut off valve 38 and the clamp 42 are opened thereby.

In keeping with a further form of the invention the photoelectric pick up 140 may have its place taken by a precision switch 148, that is joined up with the controller 146 by a wire 150. This switch 148 is as well fixed in the space 78 and more specially on the inner wall face thereof and is worked by a wave of expansion of the liner 66 moving along the length thereof as noted hereinbefore.

In the first working example of the invention, that is to say the one with a liner 66 whose wall becomes thinner from one end to the other, the photoelectric pick up 140 or the precision switch 148 are best placed at the end of the liner 66 which has the thickest wall.

On using such a control system based on changes in pressure or in volume it is naturally possible for the amount of blood kept in the pump vessel 34 to be controlled as may be desired on the condition that the pick ups used are adjusted and calibrated specially for this purpose. A further point is that a certain amount of blood may be cyclically pumped through the dialyser 40, in which respect it is not necessary for the pump vessel 34 to be pumped dry.

The shut off clamp 38 in FIGS. 1 and 6 may have a constant opening cross section or a variable one as desired, the selection in this respect being dependent on the amount of blood to be be let through on operation of the clamp. If the pressure plateau is generally level or constant, the clamp 38 will be designed with a constant opening cross section in order to get the same pumping and pressure conditions in the vein line 30. On the other hand if there is an upwardly sloping pressure plateau, that is to say in the event of there being changing pressure and pumping rate conditions while the clamp 38 is open, a form of clamp with an adjustable opening cross section will be used so as to keep the amount pumped through the vein line generally constant. This opening cross section will be controlled by a controlling unit (not figured), that may be pressure- or volume-controlled.

Such a system gives the useful effect that the pressure acting at the dialyser is not the same as the pump pressure coming into play in the pump vessel 34 and for this reason the dialyser may be run with very much lower pressures with any desired adjustment thereof in relation to the pressure in the pump vessel.

The pump vessel 34 may naturally be placed downstream from the dialyser 40 as well, that is to say in the vein line 30, there then naturally being no shut off valve 38.

A further point to be noted is that a further clamp may be placed downstream from the dialyser 40, such clamp best having a varying cross section. It will then be possible, in connection with the clamp 38, to get adjustment to any desired pressure in this branch or arm of the circuit with the dialyser therein, such pressure being less than the pressure which the apparatus is otherwise run at.

In FIGS. 7 to 9 further forms of the pump vessel 34 in keeping with the present invention will be seen to make clear, as a special point, the ways of fixing the expanding or blow up liner 66 at the end plates 46 and 48. In FIG. 7 the inner liner 66 is fixed to the end plate 46 using a locking ring 160 inside thereof and having, more specially, a coned form so as to make it simpler for this assembly to be slipped into the pocket, marked by the arrow 162 pointing towards it, in the end plate 46. The diameter of the locking ring 160 is in this respect of such a size that the opened-out end of the liner 66 is safely fixed and locked in place in the pocket.

For putting it in place, the end of the liner 66 is firstly opened out and than pulled over the end of the locking ring 160. Then this assembly is put into the pocket and fixed in position in the end plate 46. After this, the wall 68 of the pump vessel may be put in the ring-like groove 52 made for it in the end plate, and then the liner 66 is pulled through the vessel wall 68 and fixed by way of another locking ring like ring 160 in the end plate 48.

A further way of fixing the inner liner 66 in position will be seen in FIG. 8, in which case the plate 46 has a wide ring-like or annular groove 164 for the liner 66 and the further groove 52 for the wall 68 of the vessel. The liner is fixed on the collar 166 or spout of the end plate 46 within the groove 164 by way of a locking or gripping ring 168, and once again the assembly made up of the end of the liner 66 and the locking ring 168 is slipped onto the collar 166 and locked in position thereon.

Certain changes may be made in the form of the invention viewed in FIG. 3 so as to have the design viewed in FIG. 9, in which case the collar 166 has a bead 170 its lower end, the size of the bead being greater than the inner diameter of the locking ring 168. In this case the locking ring 168 is so elastic in nature that, together with the liner 66, after being stretched and slipped over the bead 170 it may be kept quite safely in place by the same.

The forms of pump vessel 46 to be seen in FIGS. 7 to 9 may naturally have the outer wall 94 as in FIG. 3 as well, that being marked by the broken lines.

Furthermore, in keeping with the preferred part of the invention, the liner 66 is placed axially in the pump vessel 34. It is best for the liner 66 to be (pre-)stretched axially by an amount equal to at least 10% of its axial length for stopping the liner 66 collapsing. In connection with the crossways or transverse stretching of the end part of the liner 66 as noted earlier one may then be certain that the liner 66 will be kept stretched out completely, without any signs of collapsing, in the pump vessel 34, inflation or expansion of the liner 66 then being more readily possible. At the same time there will be less chance of the inner wall faces of the liner 66 sticking together, when the liners are being stored, because of vulcanization.

FIG. 10 is a diagrammatic view of a pump system 180 that may be used for a normal hemodialysis unit having two needles. In such a system the blood is pumped off continuously from an artery by way of the line 26 and pumped back into a vessel by way of the line 30. Because however the pump vessel 34 may not be filled and emptied continuously at one and the same time there are, in the apparatus of FIG. 10, at least two pump vessels 182 and 184, that are worked by the pump parts 186 and 188.

In this respect the pump vessels 182 and 184 may be the same as the pump vessels in FIG. 2 or 3, while the pump parts 186 and 188 may be the same as the pump parts noted hereinbefore.

The inlet line 26 is branched at a point upstream from the two vessels 182 and 184 into at least to branch lines 190 and 192, whose outlets are joined up with two further branches 194 and 196 that come together again at a connection with the line 30. At each of the said branch points there is a switch unit 200 and 202 by which the lines 26 and 30 may be joined up with one of the lines 190 or 192, and in the other case 194 or 196. It is best for the two switch units to be put in circuit for opposite operation, that is to say operation such that when one arm of the circuit is being filled the other is being emptied, and the other way round.

The switch units 220 and 202 may be in the from of three-way valves, double clamps and the like, that are timed and kept in step with the switch-over point of the pumps 186 and 188. In is in fact possible for the these switch units to be switched over by pick ups (sensors) responsible for switching the pumps parts as well, or for them to be switched positively at the stroke-reversal point of the bellows pump parts.

A further useful effect is produced if the pumps parts 186 and 188 are united together in the form of a single pump, as for example a bellows pump whose two bellows are moved in opposite directions by a a piston rod.

It is to be noted in addition that in the pump system of FIG. 10 control may be based on pressure or on volume or furthermore it is possible to have a positive control system.

The valves or shut off valves 128 and 132 may, in keeping with a further form of the invention, be controlled without any electrical connection with the bellows pump 124 by using a mechanical driving system, for example a system using cams that are placed on the bellows or better still on the piston of the bellows pump. If adjustment of the cams is possible for changing their positions one may be certain of getting the best timing of the opening of the valves and for this reason of the pressure level in the line 122.

A special point to be kept in mind is the fact that in alarm conditions, and more specially if the pumping line 26 is pulled off at one of its ends, the artery clamp will be shut down in addition to the switching off of the most important parts of the apparatus so that there will be no danger whatsoever to the patient.

We claim:

1. A system for cleaning the blood of a patient by clearing products of metabolism from the patient's blood comprising:
    a dialyser;
    means connected to the dialyser for forming a dialysate circuit;
    means connected to the dialyser for forming a blood circuit including a blood intake, a blood outlet and means for connecting the blood intake and blood outlet to the patient's blood stream;
    means for pumping the blood through the blood circuit including a rigid casing and a flexible diaphragm within the casing, the diaphragm defining and separating a working chamber and a blood chamber which is expandable and contractable for pumping blood;
    means including a displaceable chamber for supplying the working chamber with a working fluid for expanding and contracting the working chamber so that the blood chamber is contracted and expanded;
    low pressure limiting valve means in fluid communication with the working chamber responsive to pressure within the working chamber for preventing pressure below a predetermined low pressure in the working chamber by venting the working chamber, and high pressure limiting valve means in fluid communication with the working chamber responsive to pressure within the working chamber for preventing pressure above a predetermined high pressure in the working chamber by venting the working chamber, whereby the supplying means and the blood pumping means operate in phase at pressures between the predetermined low and high pressures within completion of one cycle of expansion and contraction after start up regardless of the phase differences at start up.

2. The system as claimed in claim 1 wherein the displaceable chamber has a displacement greater than the volume able to be taken up by the working chamber in the means for pumping the blood.

3. The system as claimed in claim 2 wherein said displacement is up to 20% greater than the said volume.

4. The system as claimed in claim 1 wherein said diaphragm is in the form of a flexible tube, said casing being in the form of a hollow cylinder with end plates at ends thereof, said flexible tube being fixed into position at and between said end plates.

5. The system as claimed in claim 4 wherein said hollow cylinder has at least one port for forming a fluid connection and having a line joining said port with said supplying means.

6. The system as claimed in claim 4 wherein said casing includes an inner casing wall and a concentric outer casing wall, the tube being within the inner casing wall, a ring-like space being between the flexible tube and the inner casing wall, a further ring-like space between said inner casing wall and the outer casing wall, the two said ring-like spaces being in fluid communication with the supplying means.

7. The system as claimed in claim 5 wherein said line hollow cylinder and said supplying means has a hydrophobic diaphragm within it that covers the inner cross section of said line.

8. The system as claimed in claim 4 wherein said flexible tube is capable of undergoing at least five-fold expansion of its volume.

9. The system as claimed in claim 4 wherein said flexible tube is composed of a material selected from the group comprising: a polyurethane, unvulcanized rubber, silicone rubber, vulcanized rubber, regenerated rubber.

10. The system as claimed in claim 4 wherein the said tube has a wall becoming thinner from one end of the tube to the other.

11. The system as claimed in claim 1 further comprising a plurality of clamp means for selectively limiting flow at predetermined points in the blood circuit means, means for positively driving said supplying means between maximum and minimum volumes positions and means for clamping at least one and unclamping at least another of said plurality of clamping means at maximum and minimum volumes positions of said supplying means.

12. The system as claimed in claim 1 further comprising monitoring means for limiting the pressure and controlling the rate of fluid provided by the supplying means.

13. The system as claimed in claim 1 further comprising monitoring means for monitoring the timing and phase relationship of the low and high pressure limiting valve means and giving an alarm signal upon malfunction of said valve means.

14. The system as claimed in claim 1 further comprising a fluid line joined to the supplying means, a pressure pick up responsive to the pressure in said line, and a monitoring means for detecting, together with the pick up, a deviation in a train of pressure changes.

15. A pumping system for pumping the blood of a patient comprising:
a rigid casing and a flexible diaphragm within the casing, the diaphragm defining and separating a working chamber and a blood chamber which is expandable and contractable for pumping blood said blood chamber having blood inlet means and blood outlet means in fluid communication therewith;
means including a displaceable chamber for supplying the working chamber with a working fluid for expanding and contracting the working chamber so that the blood chamber is contracted and expanded;
low pressure limiting valve means in fluid communication with the working chamber responsive to pressure within the working chamber for preventing pressure below a predetermined low pressure in the working chamber by venting the working chamber, and high pressure limiting valve means in fluid communication with the working chamber responsive to pressure within the working chamber for preventing pressure above a predetermined high pressure in the working chamber by venting the working chamber, whereby the supplying means and the blood pumping means operate in phase at pressures between the predetermined low and high pressures within completion of one cycle of expansion and contraction after start up regardless of phase differences at start up.

16. A pumping system for pumping the blood of a patient comprising:
a rigid casing and a flexible diaphragm within the casing, the diaphragm defining and separating a working chamber and a blood chamber which is expandable and contractable for pumping blood said blood chamber having blood inlet means and blood outlet means in fluid communication therewith;
means for alternately creating a pressure above ambient pressure and a pressure below ambient pressure in the working chamber so that the blood chamber is alternately contracted and expanded;
low pressure limiting valve means in fluid communication with the working chamber responsive to pressure within the working chamber for preventing pressure below a predetermined low pressure in the working chamber by venting the working chamber to the ambient, and high pressure limiting valve means in fluid communication with the working chamber responsive to pressure within the working chamber for preventing pressure above a predetermined high pressure in the working chamber by venting the working chamber to the ambient, whereby the supplying means and the blood pumping means operate in phase at pressures between the predetermined low and high pressures within completion of one cycle of expansion and contraction after start up regardless of phase differences at start up.

* * * * *